(12) United States Patent
Yan et al.

(10) Patent No.: US 12,108,937 B2
(45) Date of Patent: Oct. 8, 2024

(54) DETECTION PACKAGE STRUCTURE WITH FLEXIBLE PRINTED CIRCUIT AND IN VIVO DETECTION APPARATUS THEREOF

(71) Applicant: INNOVEX MEDICAL CO., LTD, Shanghai (CN)

(72) Inventors: Hang Yan, Shanghai (CN); Wei Tang, Shanghai (CN); Zimei Zhang, Shanghai (CN); Ruifeng Gao, Shanghai (CN)

(73) Assignee: INNOVEX MEDICAL CO., LTD, Shanghai (CN)

( * ) Notice: Subject to any disclaimer, the term of this patent is extended or adjusted under 35 U.S.C. 154(b) by 566 days.

(21) Appl. No.: 17/312,890

(22) PCT Filed: May 21, 2019

(86) PCT No.: PCT/CN2019/087773
§ 371 (c)(1),
(2) Date: Jun. 10, 2021

(87) PCT Pub. No.: WO2020/181661
PCT Pub. Date: Sep. 17, 2020

(65) Prior Publication Data
US 2022/0061630 A1     Mar. 3, 2022

(30) Foreign Application Priority Data

Mar. 11, 2019    (CN) .......................... 201910180091.4

(51) Int. Cl.
*A61B 1/005*     (2006.01)
*A61B 1/06*      (2006.01)
*H05K 1/18*      (2006.01)

(52) U.S. Cl.
CPC ............ *A61B 1/005* (2013.01); *A61B 1/0615* (2013.01); *H05K 1/182* (2013.01); *H05K 1/189* (2013.01); *H05K 2201/10106* (2013.01)

(58) Field of Classification Search
None
See application file for complete search history.

(56) References Cited

U.S. PATENT DOCUMENTS

| | | | |
|---|---|---|---|
| 2015/0342836 A1* | 12/2015 | Allyn ..................... | A61B 1/005 600/109 |
| 2019/0021581 A1* | 1/2019 | Ishizuka .............. | H05K 3/3405 |
| 2019/0089875 A1* | 3/2019 | Fan ........................ | A61B 1/051 |
| 2020/0060521 A1* | 2/2020 | Sørensen ................ | A61B 1/05 |
| 2020/0100662 A1* | 4/2020 | Jensen ................. | A61B 1/0011 |
| 2020/0100663 A1* | 4/2020 | Jensen .............. | A61B 1/00096 |
| 2020/0194951 A1* | 6/2020 | Loo ....................... | H05K 3/3405 |
| 2020/0196434 A1* | 6/2020 | Kuo ...................... | H04N 23/57 |
| 2021/0127953 A1* | 5/2021 | Oyama ................ | A61B 1/0676 |
| 2021/0247604 A1* | 8/2021 | Endo ................... | G02B 23/2484 |

* cited by examiner

*Primary Examiner* — John P Leubecker
(74) *Attorney, Agent, or Firm* — NZ CARR LAW OFFICE (57) ABSTRACT

A detection package structure-includes an exterior tube; a detection assembly, a flexible printed circuit (FPC), a module base, and lighting members which are all disposed inside the exterior tube. The FPC includes a main flexible plate and minor flexible plates. The invention uses detection conductive materials and detection wiring parts to implement electric conduction-directed soldering, whereby to prevent from direct soldering of cables and detection assembly and enlarge soldering spots.

15 Claims, 10 Drawing Sheets

DETECTION PACKAGE STRUCTURE WITH FLEXIBLE PRINTED CIRCUIT AND IN VIVO DETECTION APPARATUS THEREOF

FIELD OF THE INVENTION

The present invention relates to the field of medical treatment, more specifically to a detection package structure and an in vivo detection apparatus.

BACKGROUND

With advance of medical science, the flexible tube-based in vivo detection technology has been widely applied to medical treatment. Thereby, the medical personnel can inspect human organs by inserting the flexible tube-based in vivo detection apparatus into human bodies.

In the related techniques, a flexible tube-based in vivo detection apparatus includes a flexible and controllable curved tube and an insertion member. The insertion member is formed on one side of the flexible and controllable curved tube and contains a detection member. A wiring terminal of the detection member may be soldered to cables to facilitate electric conduction.

However, since the detection member becomes miniature, the cables of the detection member do as well, which results in complicating operation during the soldering process with other cables. Thus, the soldering effect is hard to guarantee. In addition, the flexible and controllable curved tube bends during operation, which might wrench wires of the detection member and then affect stability and safety of conduction. Although the standards strictly demand the process and quality of the packaging of the insertion member, the current packaging technology is hardly able to meet the requirement.

SUMMARY

The present invention provides a detection package structure and an in vivo detection apparatus to overcome the soldering difficulty and solve the problems of stability and safety of electric conduction due to wrenched wires.

According to a first aspect, the present invention provides a detection package structure. The package structure comprises an exterior tube, a detection assembly, a flexible printed circuit (FPC), a module base, and lighting members, wherein the detection assembly, the FPC, the module base, and the lighting members are deposed inside the exterior tube. The FPC further comprises a main flexible plate and two minor flexible plates, and the minor flexible plates respectively connect with two opposite edges of the main flexible plate. The exterior tube connects with a flexible and controllable curved tube. The main flexible plate and the detection assembly are deposed on a first side of the module base; the front side of the main flexible plate is connected with the rear side of the detection assembly; the surface of the main flexible plate is provided with detection conductive materials soldered to the detection assembly for electric conduction; and the detection conductive materials is further soldered to a detection wire of a cable for electric conduction via a detection wiring part. When being bent to desired positions, the minor flexible plates are respectively on a second side and a third side of the module base, which are opposite to each other. The end of the minor flexible plates is provided with the lighting members and extends forward to a position near the front side of the detection assembly.

Alternately, the surface of the minor flexible plates are provided with a illumination conductive material, the illumination conductive material is soldered to the lighting members for electric conduction to configure two of the lighting members in parallel, and the illumination conductive material is soldered to an illumination wire of the cable for electric conduction via an illumination wiring part; and the illumination wiring part is deposed on the main flexible plate.

Alternately, the minor flexible plates further comprise a first plate body connected to the main flexible plate, a second plate body connected to the front side of the first plate body, and a third plate body connected to the front side of the second plate body, wherein the lighting member is deposed on the third plate body, and wherein when the first plate body, the second plate body, and the third plate body are bent to desired positions, the first plate body and the second plate body of one of the minor flexible plates connect to the second side of the module base, and the first plate body and the second plate body of another one of the minor flexible plates connect to the third side of the module base, and wherein the third plate body of the minor flexible plates is positioned on one side of the front side of the module base, and wherein two of the third plate bodies are deposed opposite to each other and two of the first plate bodies are deposed opposite to each other.

Alternately, if the lighting members are deposed on the surface of a side of the third plate body which faces another one of the third plate bodies, the gap between two of the third plate bodies matches the corresponding-direction size of the detection assembly and that of the lighting members;

if the lighting members are deposed on the surface of a side of the third plate body which does not face another one of the third plate bodies, the gap between two of the third plate bodies match the corresponding-direction size of the detection assembly.

Alternately, the first side of the module base has a detection positioning part for positioning and installing the detection assembly;

a fourth side of the module base corresponding to the first side thereof has an instrument tube channel for passing through an instrument tube;

the second side and the third side of the module base has a flexible plate channel for accommodating at least a portion of the minor flexible plates.

Alternately, the detection assembly further comprises a detection member, a wiring terminal of the detection member is directly or indirectly connected with the main flexible plate for electric conduction, and the detection member is fixed to the module base.

Alternately, the detection assembly further comprises a detection circuit board, a first conductive material deposed on a first side of the detection circuit board, and a second conductive material deposed on a second side of the detection circuit board, wherein the detection circuit board is deposed in a vertical direction on the first side of the module base; the detection member is deposed on the first side of the detection circuit board; the wiring terminal of the detection member is soldered to the first conductive material for electric conduction; the front side of the main flexible plate is connected to the rear side of the detection circuit board; the detection conductive materials are soldered to the second conductive material for electric conduction.

Alternately, at least a portion of the outer edge of the detection circuit board and at least a portion of the outer edge of the module base are in the shape of circular arc, matching the inner wall of the exterior tube.

Alternately, the main flexible plate and/or the minor flexible plates are bonded to the module base with glue.

According to a second aspect, the present invention further provides an in vivo detection apparatus, comprising:

a flexible and controllable curved tube and the detection package structure above-mentioned, wherein the detection package structure forms an insertion portion at one side of the controllable curved tube.

The detection package structure and the in vivo detection apparatus of the present invention achieve the followings: preventing from direct soldering of the cables and the detection assembly with the main flexible plate of the FPC and the detection assembly; and using the detection conductive materials and the detection wiring part on the main flexible plate to advance enlargement of soldered joints compared to soldering between wirings.

Thus, the present invention simplifies soldering operation and enhances the strength and reliability of soldering, which thereby provides desired stability in different motion conditions.

In addition, the present invention utilizes FPC to assure conductive connection for carrying out assembly. Specifically, because having flexibility, FPC is less likely to suffer conductive connection degrading caused by size errors or external force and thereby improves the stability of conductive connection.

The present invention and its alternatives may minimize the size of the package structure in radial direction by bending the FPC.

In an alternative, the present invention can prevent from direct soldering of the cables and the detection assembly via soldering the detection conductive materials to the wiring terminal which are between the detection member and the detection circuit board. In addition, the detection member merely needs to be soldered to the lateral-side first conductive material, which favors enlargement of soldered joints of the detection member as well. Thus, the present invention simplifies soldering operation and enhances the strength and reliability of soldering, which thereby provides desired stability in different motion conditions.

In an alternative of the present invention, with the instrument tube channel, the flexible plate channel, and the detection positioning part formed on the module base, the following functions are achieved: simplifying installation, increasing positioning precision, and improving connection strength. Thus, the installed detection member is unlikely to be affected by external force.

BRIEF DESCRIPTION OF THE DRAWINGS

To describe the technical solutions in the embodiments of the present invention more clearly, the following briefly describes the accompanying drawings required for describing the embodiments or the prior art. Apparently, the accompanying drawings in the following description show merely some embodiments of the present invention, and a person of ordinary skill in the art may still derive other drawings from these accompanying drawings without creative efforts.

DESCRIPTION OF REFERENCE NUMERALS

1—FPC board;
11—main flexible plate;
111—detection conductive materials;
112—detection wiring parts;
113—illumination wiring part;
12—minor flexible plate;
121—first plate body;
122—second plate body;
123—third plate body;
2—detection assembly;
21—detection member;
22—detection circuit board;
3—module base;
31—detection positioning part;
32—flexible plate channel;
33—instrument tube channel;
4—instrument tube;
5—lighting members;
6—exterior tube.

DETAILED DESCRIPTION OF THE EMBODIMENTS

The technical schemes in the embodiments of the present invention will be described clearly and fully in cooperation with the attached drawings. It is obvious that the embodiments described in the specification are not the total embodiments of the present invention but only a portion of the embodiments. The embodiments derived by the persons having ordinary knowledge in the field without creative effort would be also included by the scope of the present invention.

The ordinal numbers, such as "first", "second", "third" and "fourth appearing in the specification, claims, and drawings of the present invention are not necessarily used to indicate the order or priority of objects but only used to distinguish similar objects. It should be understood: the ordinal numbers are interchangeable in such a case. Thus, the present invention may be practiced in an order different from the order indicated by the ordinal numbers appearing the specification or drawings. The terms "comprise" and "have" and other equivalent variants thereof are used to indicate that the subject covers the objects but does not exclude other things. For example, a process, method, system, product or apparatus may include a series of steps or units. However, the description does not necessarily list all the steps or units clearly. In such a case, "comprise" or "have" may be used to cover some of the steps or units but does not exclude other steps or units.

Below, embodiments will be used to demonstrate the technical schemes of the present invention in detail. Further, the embodiments described below may be integrated together to form new embodiments. Besides, identical or similar concepts or processes that have been described in some embodiments may not repeat in other embodiments.

Figure 1:
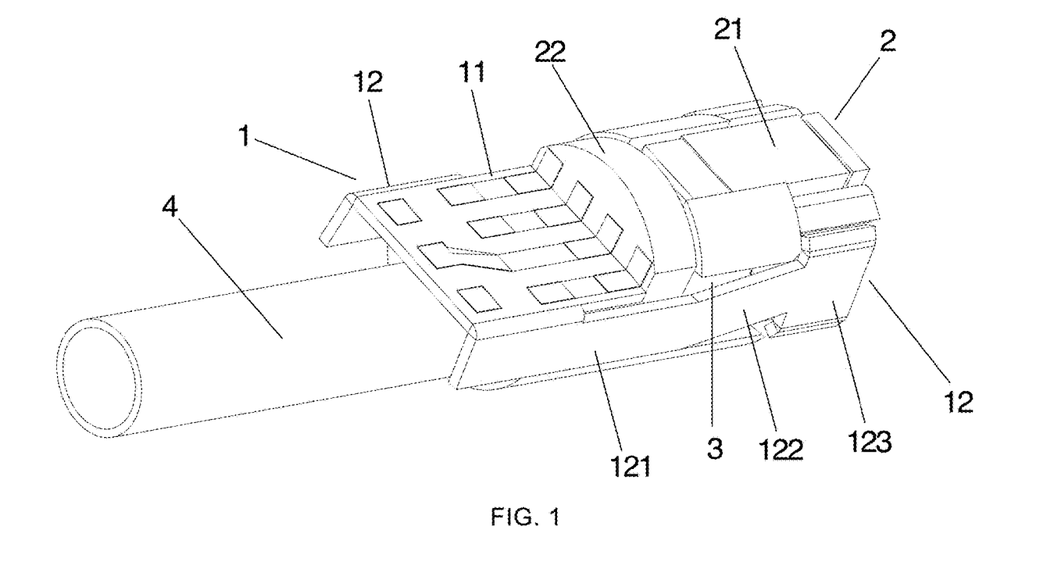
FIG. 1 is a first structure schematic diagram of a detection package structure according to an embodiment of the present invention.
Figure 2A:
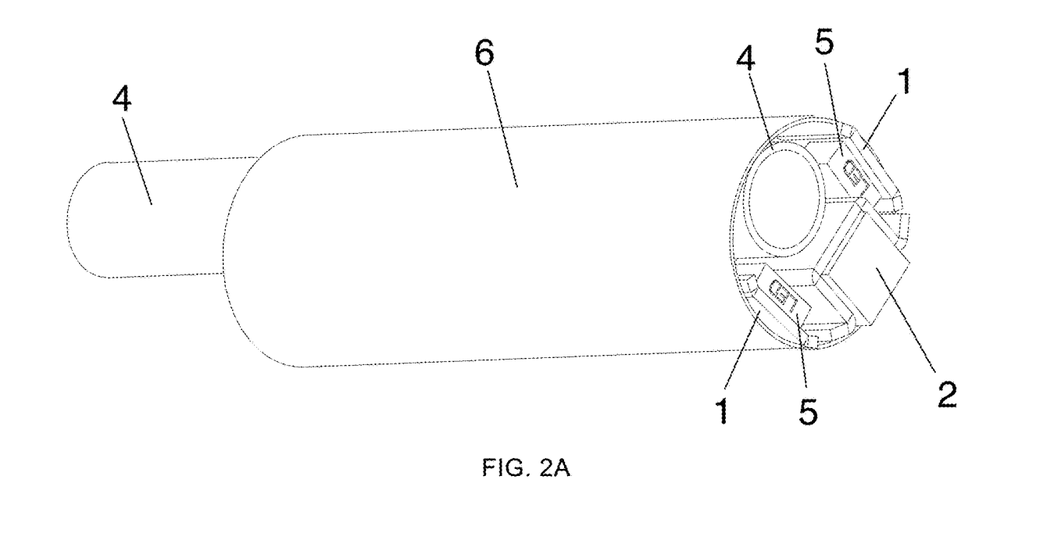
FIG. 2A and FIG. 2B illustrate a second structure schematic diagram of a detection package structure according to an embodiment of the present invention.
Figure 2B:
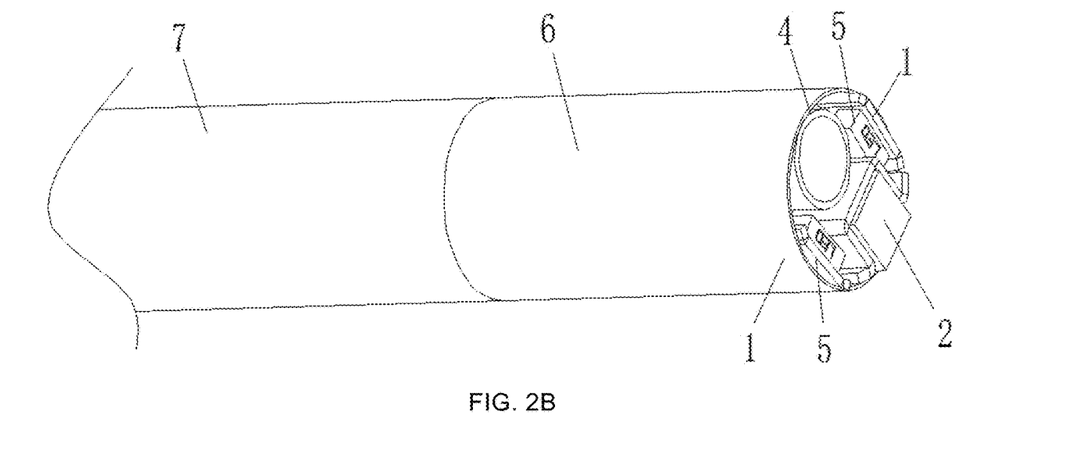
Figure 3:
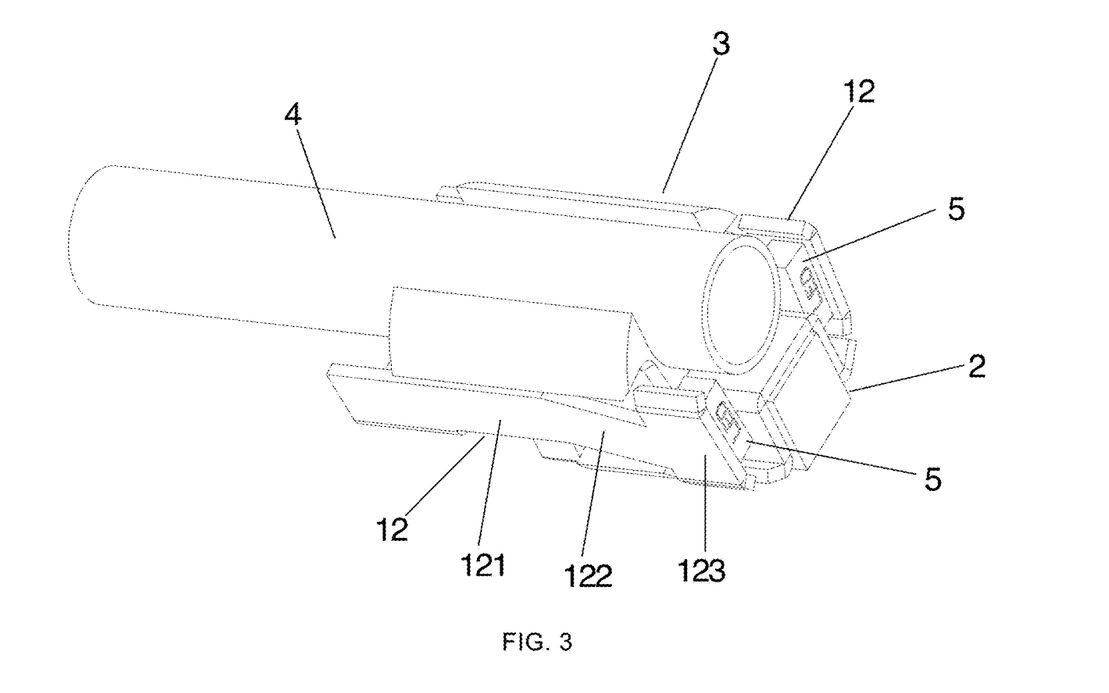
FIG. 3 is a third structure schematic diagram of a detection package structure according to an embodiment of the present invention.

FIG. 1 is a first structure schematic diagram of a detection package structure according to an embodiment of the present invention; FIG. 2A and FIG. 2B illustrate a second structure schematic diagram of a detection package structure according to an embodiment of the present invention; FIG. 3 is a third structure schematic diagram of a detection package structure according to an embodiment of the present invention; and FIG. 4 is a fourth structure schematic diagram of a detection package structure according to an embodiment of the present invention;

Referring to FIG. 1 to FIG. 4, the detection package structure includes: an exterior tube 6; and a detection assembly 2, an FPC board 1, a module base 3, and lighting members 5, wherein the detection assembly 2, the FPC 1, the module base 3, and the lighting members 5 are deposed inside the exterior tube 6. The FPC 1 includes a main flexible plate 11 and two minor flexible plates 12. The minor flexible plates 12 are respectively connected with two opposite edges of the main flexible plate 11.

The detection assembly 2 may be understood as an assembly of the members containing detection-related elements. The detection assembly 2 may face forward. Thus, in this embodiment and other embodiments, the front side and rear side are defined according to the forward direction of the detection assembly 2. In other words, the front side of any member refers to the side of the detection assembly 2 which is in the forward direction and the rear side of any member refers to the side of the detection assembly 2 which is in the backward direction.

Figure 4:
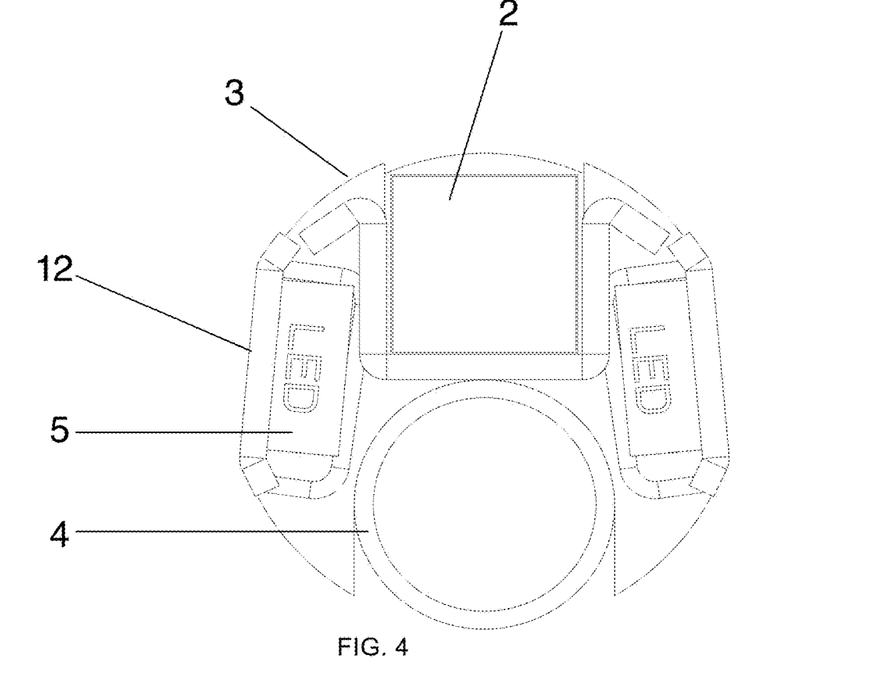
FIG. 4 is a fourth structure schematic diagram of a detection package structure according to an embodiment of the present invention.

The main flexible plate 11 and the detection assembly 2 are deposed on a first side of the module base 3 which may be an upper side, as shown in FIG. 4. The front side of the main flexible plate 11 is connected to the rear side of the detection assembly 2.

Figure 5A:
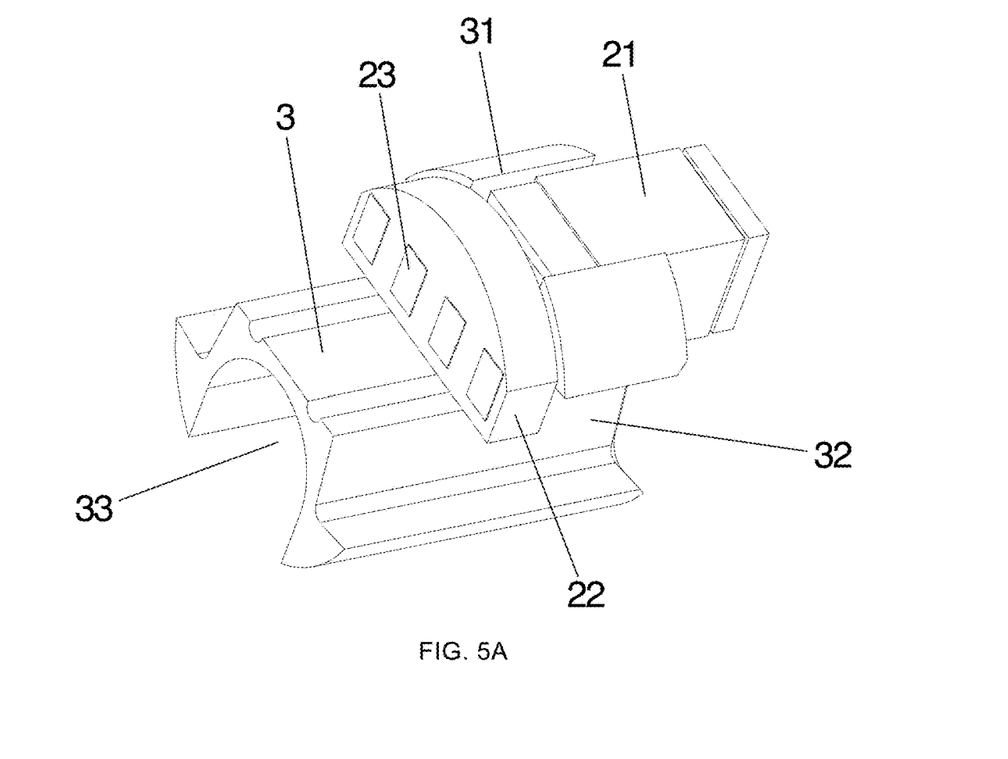
FIG. 5A and FIG. 5B illustrate a structure schematic diagram of a detection assembly and a module base according to an embodiment of the present invention.
Figure 5B:
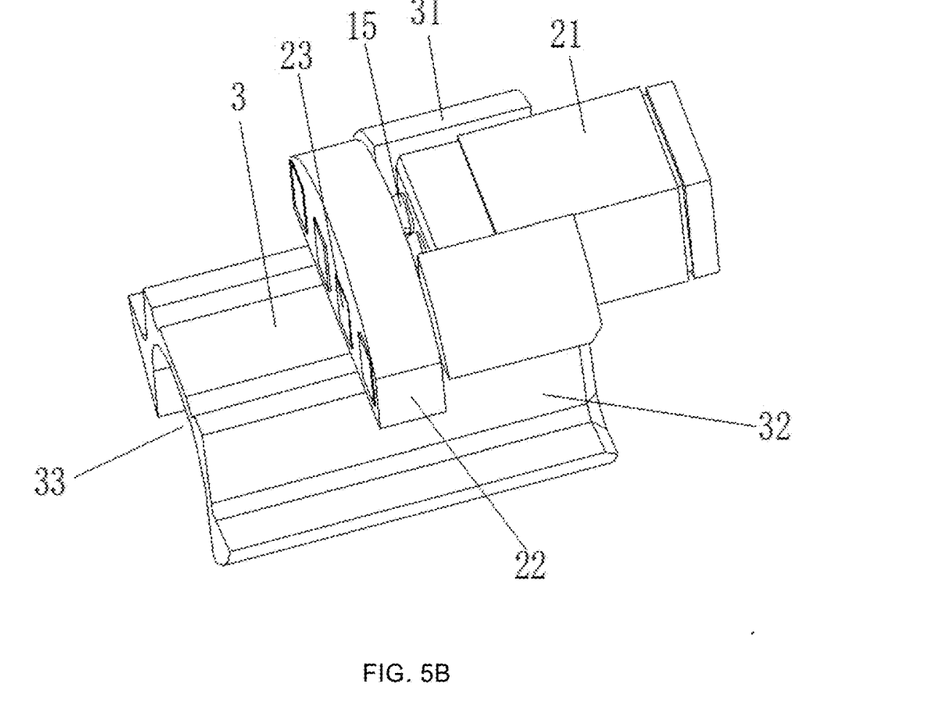
Figure 6:
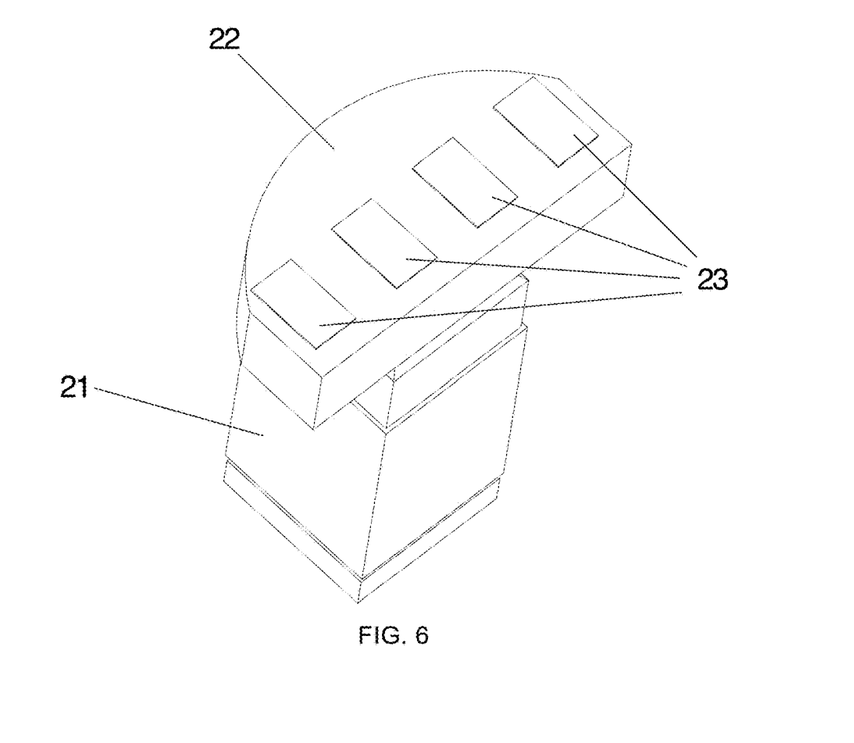
FIG. 6 is a structure schematic diagram of a detection assembly according to an embodiment of the present invention.

FIG. 5A and FIG. 5B illustrate a structure schematic diagram of a detection assembly and a module base according to an embodiment of the present invention. FIG. 6 is a structure schematic diagram of a detection assembly according to an embodiment of the present invention. FIGS. 7A-7D illustrate a structure schematic diagram of an FPC according to an embodiment of the present invention;

In this embodiment, the surface of the main flexible plate 11 has detection conductive materials 111 conductively soldered to the detection assembly 2, and the detection conductive materials 111 are also to be soldered to detection wires 9 of cables for electric conduction 8 via the detection wiring parts 112.

The detection conductive material 111 and the detection wiring part 112 may be any materials that can realize electric conduction-directed soldering. Specifically, the detection conductive material 111 is connected with a conductive material on the detection assembly 2, and the detection wiring part 112 is connected with a detection wire 9 of cables, the detection conductive material 111 can conduct with the detection wiring part 112. Therefore, signaling and/or power transmission between detection wires 9 of cables and the detection circuit board 22 are achieved. The detection conductive material 111 and the detection wiring part 112 may be copper sheet for instance.

In a specific implementation process, the detection conductive materials 111 may be in parallel.

The main flexible plate of the FPC and the detection assembly of the present invention can prevent the cables and the detection assembly from direct soldering therebetween. In addition, comparing with soldering between wires, utilizing the detection conductive materials and the detection wiring parts on the main flexible plate favors enlarging soldering joints. Therefore, the present invention can reduce the difficulty of soldering operation, increase the strength and reliability of soldering joints and enhance the stability of electric conduction-directed soldering in various dynamic states.

In one of embodiments, the detection assembly 2 includes a detection member 21, wherein a wiring terminal 15 of the detection member 21 is directly or indirectly connected with the main flexible plate for electric conduction. The detection member 21 is fixedly connected with the module base 3. By this embodiment, electric connection and component mounting can be achieved.

In a detailed example, the detection assembly 2 further includes a detection circuit board 22, a first conductive material (not shown in the figures) deposed on a first side of the detection circuit board 22, and a second conductive material 23 deposed on a second side of the detection circuit board 22.

The detection circuit board 22 is deposed in a vertical direction on a first side of the module base 3. The detection member 21 is deposed on a first side of the detection circuit board 22, and the wiring terminal 15 of the detection member 21 is soldered to the first conductive material for electric conduction. The front side of the main flexible plate 11 is connected to the rear side of the detection circuit board 22. The detection conductive material 111 is soldered to the second conductive material 23 for electric conduction.

The design of the main flexible plate, the detection circuit board that is perpendicular to the main flexible plate, and the conductive material thereon prevents cables and the detection member from direct soldering. In addition, the detection member merely needs soldering to the first conductive material on the lateral side. Then is enlarged the solder points of the detection member. Therefore, the present invention can reduce the difficulty of soldering operation, increase the strength and reliability of soldering joints and enhance the stability of electric conduction-directed soldering in various dynamic states.

While a first side and a second side of the detection circuit board 22 may be planar, these sides may also be curved or circular arc in this embodiment.

The first conductive material may be any material that can realize electric conduction-directed connection, such as copper sheet. In one of embodiments, the first conductive material may be deposed on the surface of the detection circuit board 22. In alternate embodiments, the first conductive material may be deposed on a recess formed on the surface of the detection circuit board 22.

The second conductive material 23 may be any material that can realize electric conduction-directed connection, such as copper sheet. In one of embodiments, the second conductive material 23 may be deposed on the surface of the detection circuit board 22. In alternate embodiments, the second conductive material 23 may be deposed on a recess formed on the surface of the detection circuit board 22.

In one of embodiments, the detection member 21 and the module base 3 are bonded to each other with glue, and thus the detection member 21 and the module base 3 are bonded as a rigid body. By fastening the position of the detection assembly 2, connection strength between the detection member and the detection circuit board 22 is improved. Thus, separation of the detection member and the detection circuit board 22 is prevented.

In a detailed embodiment, the detection member 21 may include sensors, and the detection circuit board 22 may be a printed circuit board (PCB).

In one of embodiments, at least a portion of the outer edge of the detection circuit board 22 and at least a portion of the outer edge of the module base 3 are in the shape of a circular arc, matching the inner wall of the exterior tube. Furthermore, the detection circuit board 22 may be in the shape of a semicircular arc or an approximately semicircular structure.

In another embodiment, the detection member 21 may also be directly soldered to the main flexible plate 11 for electric conduction. For instance, the wiring terminal 15 of the detection member 21 may be directly soldered to the detection conductive material 111 of the main flexible plate 11 for electric conduction. In the light of this embodiment, the detection circuit board 22 may not be used, and the detection member 21 may be bonded onto the module base 3 with glue.

In this embodiment, the exterior tube 6 may be connected to a flexible and controllable curved tube 7.

In one of embodiments, the exterior tube 6 may be filled with glue. With the glue, fixing between PCBs, members, and instruments is achieved, and the packaging of the entire device is done. "Filled with glue" can be understood as that no matter the exterior tube 6 filled with glue is fully or partly, the above-mentioned embodiments are applicable.

The detection member 21 may be an image capture member, and the detection assembly 2 may be an image capture assembly. In alternate embodiments, the detection member 21 may be a sensing device for detecting physical properties or chemical properties of liquid, gas, or solid, such as a liquid sensing device, a gas sensing device, etc.

The detection member 21 may be an image capture member. As having been developed rapidly, image sensors may have a miniature size of 0.7 mm*0.7 mm. Therefore, there is an urgent demand for a package structure that is able to control the outer diameter, with lighting members, safe and reliable in package, and economical. The device provided by this embodiment and its alternatives exactly meet the requirement.

If the detection member 21 is a sensor, it may include a chip and a camera and may be in form of a cuboid structure, as shown in the figure. Besides, the detection member 21 may further include a detection member frame on which the sensor may be deposed.

To realize effective image capturing, the structure may utilize a lighting member 5 for illuminating, and the orientation of the lighting member 5 is identical to the orientation of the detection member 21.

In this embodiment, when two minor flexible plates 12 are bent to a desired position to facilitate installation of the lighting member 5, the two minor flexible plates 12 are respectively on a second side and a third side of the module base 3, which are opposite to each other. The minor flexible plates 12 and the main flexible plate 11 are flexible and may be configured to bend to each other. In an example, the aforementioned bending may be unidirectional or bidirectional. In an example, the aforementioned bending may be realized via designing the joints to be thinner structures. In another example, the flexible plates themselves are sufficient to realize bending, and additional structures suitable for bending are unnecessary. In other words, the minor flexible plate 12 may be understood as a part of the FPC which can be bent to the second side or the third side of the module base 3 for positioning and installing the lighting member 5.

In this embodiment, the end of the minor flexible plate 12 has the lighting member 5. Because the minor flexible plate 12 is connected with the main flexible plate 11, a position that is remote from the junction can be understood as the end of the minor flexible plate 12. The end of the minor flexible plate 12 is forwardly extended toward to a position approximating to the front side of the detection assembly 2.

With the minor flexible plate 12, the lighting member 5 is suitable to be deposed on the detection member 21 and thereby contributes sufficient and effective illuminating toward desired detection directions. The lighting member 5 and the detection member 21 may be planar on the same reference plane, which favors uniformly illuminating. The reference plane may be understood as a plane perpendicular to the desired detection direction.

The lighting member 5 may be any optical component that can output light, such as LED. The present invention does not limit that the lighting member 5 should output a specified color or should operate according to a specified principle. In a detailed embodiment, the lighting member 5 may project monochromatic light, dichromatic light, or light that changes color.

An adhesive sheet is applicable for deposing the lighting member 5 on the minor flexible plates 12, and more specifically, the adhesive sheet is deposed on the third plate body 123 of the minor flexible plates 12.

The bent LEDs are symmetrically arranged on the both sides of the detection member (such as sensor). In addition, the bent LEDs and the end of the detection member are on the same plane. In this way, uniform illumination is achieved.

Figure 7A:
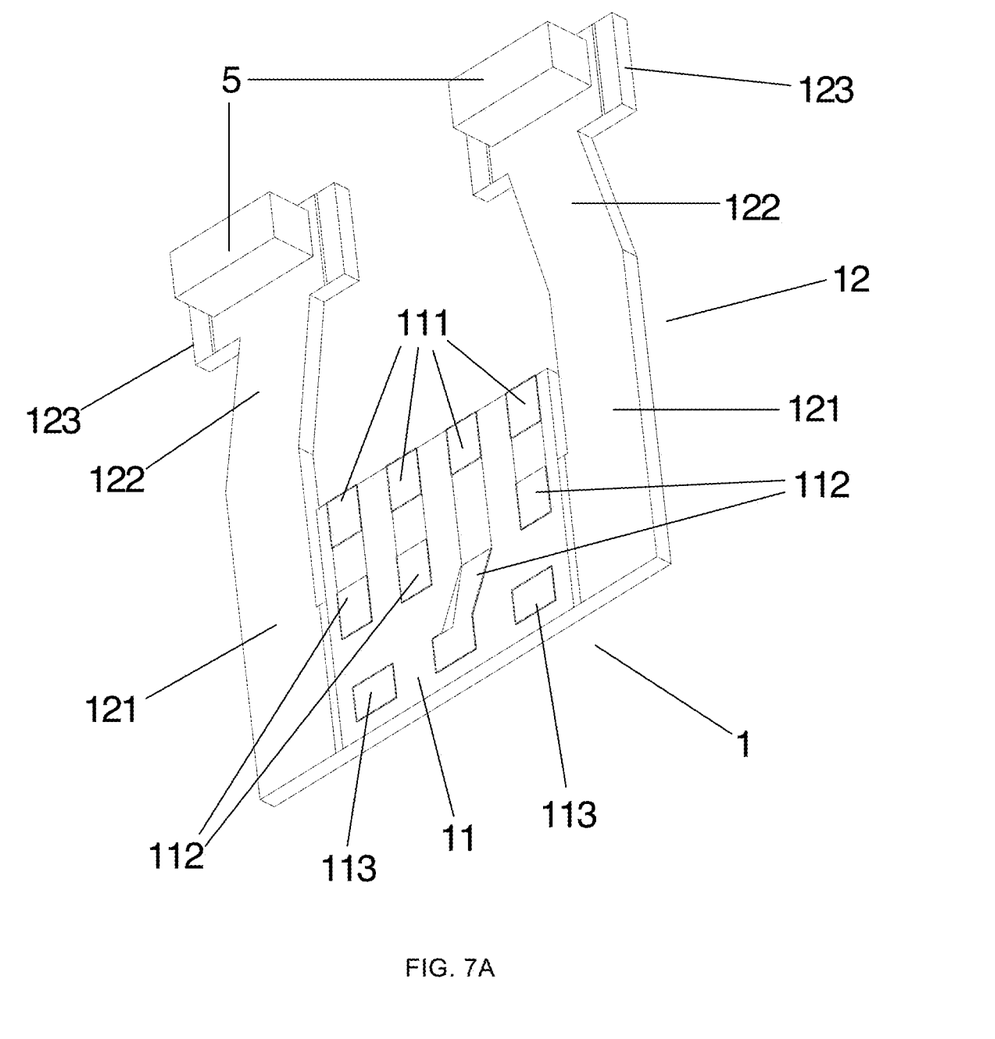
FIGS. 7A-7D illustrate a structure schematic diagram of an FPC according to an embodiment of the present invention.
Figure 7B:
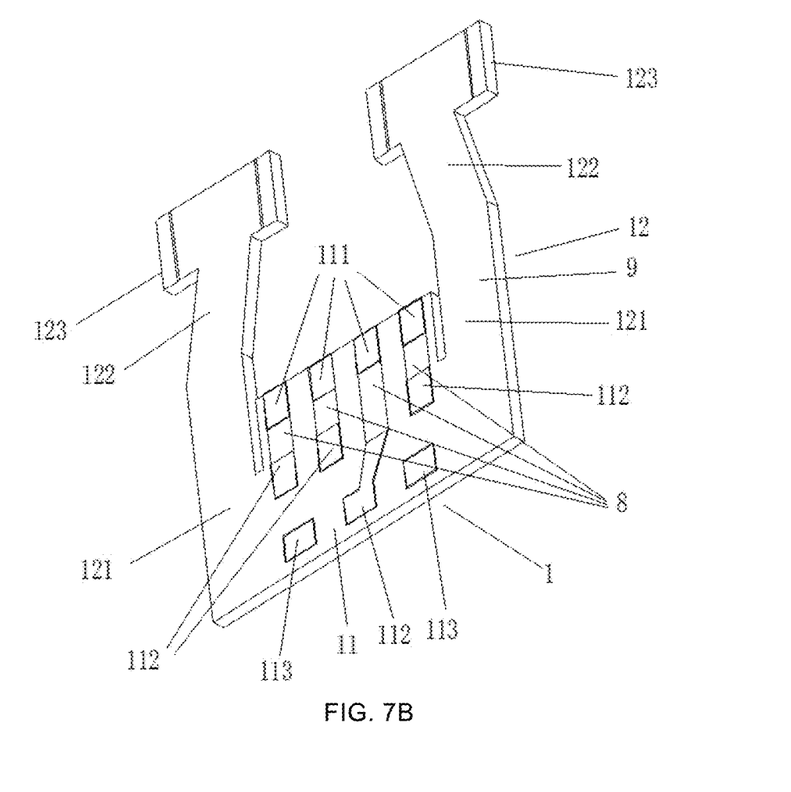
Figure 7C:
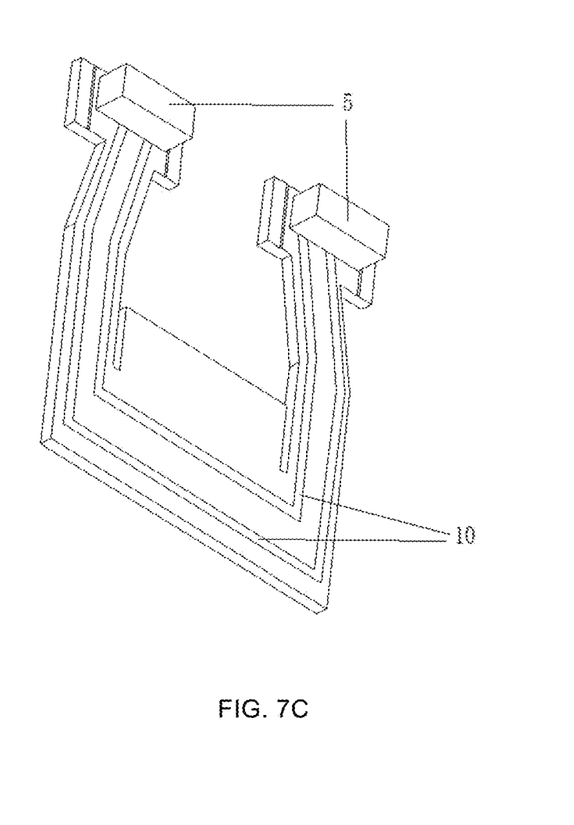
Figure 7D:
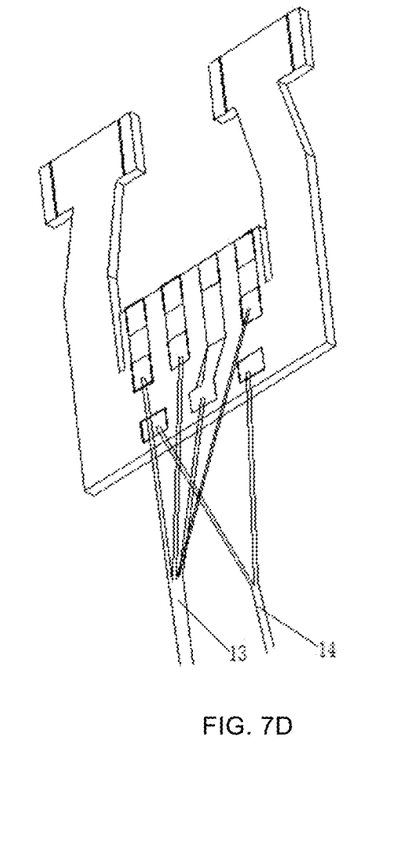

In one of embodiments, the surface of the minor flexible plates 12 has illumination conductive materials 10 (shown in FIG. 7C). The illumination conductive materials 10 are soldered to the lighting members 5 for electric conduction, and thereby two of the lighting members 5 are in parallel. The illumination conductive materials 10 are also soldered to the illumination wires 14 of cables for electric conduction 13 via the illumination wiring part 113. The illumination wiring part 113 is deposed on the main flexible plate 11.

The illumination conductive material 10 may be any material facilitating connection and electric conduction. Specifically, the illumination conductive material 10 is a conductive material able to facilitate the connection and electric conduction with the lighting members 5 and the illumination wiring part 113. Therefore, signaling and/or power transmission between illumination wires 14 of cables and the lighting members 5 are achieved. For instance, the conductive material for illuminating may be a metal sheet such as copper sheet. The illumination wiring part 113 may be any material able to facilitate soldering and electric conduction, such as copper sheet.

In one of the embodiments, the minor flexible plates 12 includes a first plate body 121 connected to the main flexible plate 11; a second plate body 122 connected to the front side of the first plate body 121; and a third plate body 123 connected to the front side of the second plate body 122. The lighting member 5 is deposed on the third plate body 123.

The first plate body 121 may be bent with respect to the main flexible plate 11; the second plate body 122 may be bent with respect to the first plate body 121; the third plate body 123 may be bent to the second plate body 122. The method to carry out the aforementioned bending may be in accordance with the bending between the main flexible plate 11 and the minor flexible plates 12 described hereinbefore.

When the first plate body 121, the second plate body 122, and the third plate body 123 are bend to desired positions, the first plate body 121 and the second plate body 122 of one of the minor flexible plates 12 are connect to the second side of the module base 3, and the first plate body 121 and the second plate body 122 of another one of the minor flexible plates 12 are connected to the third side of the module base 3. The third plate body 123 of the minor flexible plates 12 is positioned on the front side of the module base 3. In other words, the third plate body 123 extends to the outside of the module base 3.

When being bended to desired positions, the two third plate bodies 123 are deposed oppositely, and the two first plate bodies 121 are also deposed oppositely. In this way, it is guaranteed that two sides of the detection assembly 2 are symmetrical. Thus, the present invention can provide uniform illumination for detection.

In one of the embodiments, as shown in FIGS. 7A-7D, when not being bent, the FPC may be in form of a U-shape structure, and one surface thereof may have the detection conductive material 111.

When the FCP is not bent, the gap between the two first plate bodies 121 may be different from the gap between the two third plate bodies 123; for example, the gap between the two first plate bodies 121 is larger than the gap between the two third plate bodies 123. Thus, after the FCP is bent, this arrangement contributes causing position offset in a direction of the third plate bodies 123 corresponding to the first plate bodies 121, wherein the direction is perpendicular to the desired detection direction. For instance, after the third plate bodies 123 and the first plate bodies 121 have been bent to a desired position, a position offset is caused in a direction, wherein the direction is between the first plate bodies 121 and the corresponding third plate bodies 123 and is along from the fourth side of the module base 3 to the first side of that. In this way, the arrangement contributes making the lighting member 5 on the third plate body 123 closer to the detection assembly 2 and thereby provides precise and effective illuminating.

Referring the FIG. 1 to FIG. 4, if the lighting members 5 are respectively deposed on a first surface of one third plate body 123 and a second surface of the other third plate body 123, wherein the first surface faces the second surface, it means that when the third plate bodies 123 are bent to desire positions, the lighting members 5 are deposed respectively on the surfaces of the two third plate bodies 123, which face each other, and the gap between the two third plate bodies 123 matches the corresponding-direction size of the detection assembly 2 and that of the lighting members 5. The aforementioned matching may be understood as: since the detection assembly 2 and the lighting members 5 are positioned between the two third plate bodies 123, then the gap between the two third plate bodies 123 may be increased according to the size of the detection member 21 of the detection assembly 2 and/or to the size of the lighting members 5. In addition, the aforementioned matching may be equal or unequal.

Figure 10:
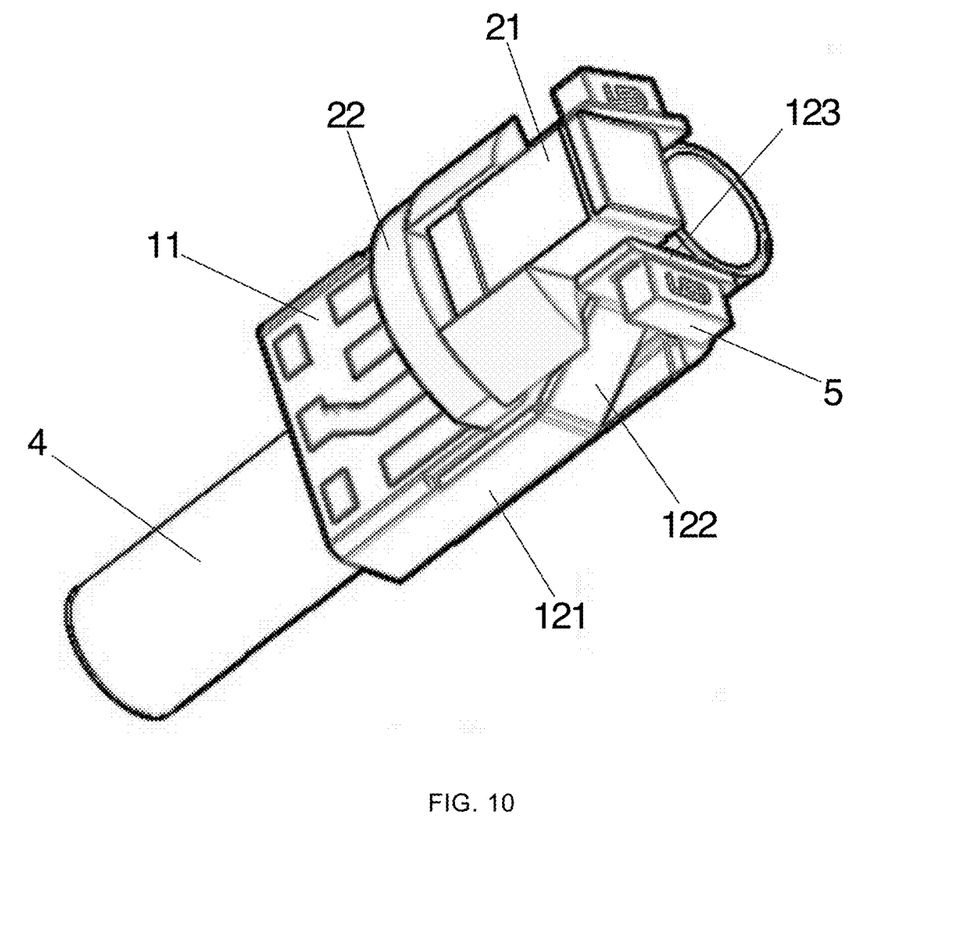
FIG. 10 is a fifth structure schematic diagram of a detection package structure according to an embodiment of the present invention.

FIG. 10 is a fifth structure schematic diagram of a detection package structure according to an embodiment of the present invention.

Referring to FIG. 10, if the lighting members 5 are respectively deposed on a third surface of one third plate body 123 and a fourth surface of the other third plate body 123, wherein the third surface does not face the fourth surface, it means that when the third plate bodies 123 are bent to desire positions, the lighting members 5 are deposed respectively to the surfaces of the two third plate bodies 123, which do not face each other, and the gap between the two third plate bodies 123 matches the corresponding-direction size of the detection assembly 2. The aforementioned matching may be understood as: since the detection assembly 2 is positioned between the two third plate bodies 123 and the lighting members 5 is not positioned between the two third plate bodies 123 then the gap between the two third plate bodies 123 may be increased according to the size of the detection member 21 of the detection assembly 2. In addition, the aforementioned matching may be equal or unequal.

In the embodiment, therefore, by bending the FPC, the size of the package structure in radial direction is likely to be minimized. Specifically, the FPC may be understood as a FPC board having a thickness of 0.15 mm and being foldable. With FPC board, the packaged size in radial direction of the detection member and the lighting members is effectively controllable, required precision of size for manufacture and installation is facilitated, and durability to external force during installation is improved.

By utilizing FPC, this embodiment assures conductive connection favors carrying out assembly. In addition, because having flexibility, FPC is unlikely to suffer degrading of conductive connection caused by size error or external force and thereby improves the stability of conductive connection.

Figure 8:
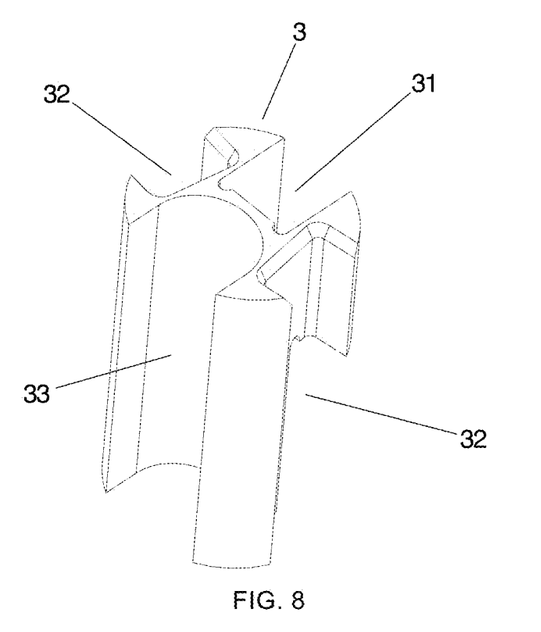
FIG. 8 is a first structure schematic diagram of a module base according to an embodiment of the present invention.
Figure 9:
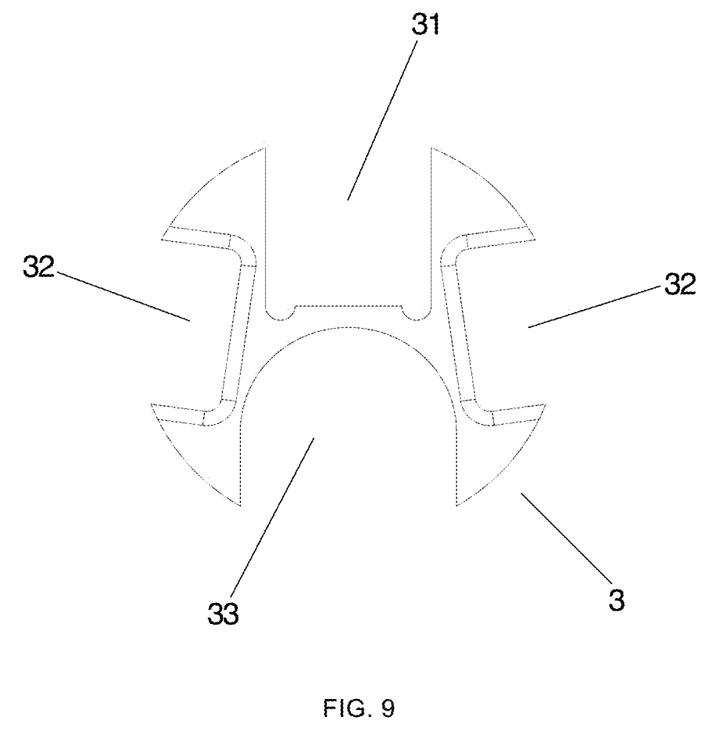
FIG. 9 is a second structure schematic diagram of a module base according to an embodiment of the present invention.

Referring to FIG. 8 and FIG. 9 and combining FIG. 4 with FIG. 5A and FIG. 5B, the first side of the module base 3 has a detection positioning part 31 for positioning and installing the detection assembly 2. The fourth side of the module base 3, which is corresponding to the first side thereof, has an instrument tube channel 33 for passing through an instrument tube 4. The second side and the third side of the module base 3 have a flexible plate channel 32 for accommodating at least a portion of the minor flexible plates 12.

The detection positioning part 31 may include two positioning bosses extending externally. The gap between the two positioning bosses may match the corresponding-direction size of the detection member 21 so that the detection member 21 may pass through the gap between the two positioning bosses. Meantime, the gap between the two positioning bosses may be smaller than the corresponding-direction size of the detection circuit board 22 so that the detection circuit board will not pass through the gap. Therefore, with the detection positioning part 31, fastening the detection assembly 2 in a limited position is achieved.

The instrument tube channel 33 mentioned above may be any shape matching the instrument tube 4. The flexible plate channel 32 may be any structure channel which the detection member 12 may pass through.

With the above-mentioned design, the module base 3 may be an H-shaped structure, which may be made of metal. Referring an example shown in FIG. 9, the detection assembly 2 and the instrument tube 4 are respectively and symmetrically arranged on the upper side and the lower side of the H-shaped structure. The side of the module base 3 has flexible plate channels 32 including a planar positioning edge structure for the FPC 1 and the detection circuit board 22. In consequence, the following functions are achieved: simplifying installation; increasing positioning precision; preventing the installed detection member from being affected by external force; improving reliability and soldering strength of the detection member, the LEDs, and the cables; and reducing a short-circuit risk of the solder points and the outer tube.

Besides, the outer edge of the positioning bosses may be in the shape of a circular arc matching the exterior tube 6.

With the detection positioning part, the instrument tube channel, and the flexible plate channel formed on the module base, the following functions are achieved: simplifying installation; increasing positioning precision; and improving connection strength. Therefore, the installed detection member is unlikely to be affected by external force.

In embodiments, the main flexible plate 11 and/or the minor flexible plates 12 are bonded to the module base 3 with glue. Thus, even if the cables are pulled in axial direction, the connection strength is still reliable.

In one embodiment, the instrument tube 4 may be a flexible circular tube structure. After being installed in a metallic exterior tube and being fixed with glue together with other elements, the instrument tube 4 and those elements form an endoscope insertion unit. The cables may be multicore coaxial cables with shield layers. The shied layers may enhance soldering strength as well as exempt the cables from abnormalities.

The present invention also provides an in vivo detection apparatus, which comprises the aforementioned package structures of a detection and the aforementioned flexible and controllable curved tube. The detection package structure has an insertion member at one end thereof.

The insertion member and the controllable curved tube may respectively function as the insertion member and the controllable curved tube of the endoscope device.

In some embodiments of the present invention, the aforementioned structure and device and the modified structure thereof may be used to form a package of an insertion member of a micro sensor, wherein the packaged insertion member has a diameter of 2-10 mm. Thus is greatly expanded the application field of a micro sensor to the endoscope.

In conclusion, the present invention proposes a detection package structure and an in vivo detection apparatus, wherein the design of the main flexible plate and detection assembly on the FPC can prevent the cables from being directly soldered to the detection assembly, and wherein the detection conductive material of the main flexible plate and the detection wiring part are used to implement soldering. In comparison with the cable-to-cable soldering technology, the present invention favors enlarging soldering spots. Therefore, the present invention can lower the difficulty of soldering operation, enhance the strength and reliability of soldering, and promote the stability of the electric conduction-directed soldering in various dynamic states.

Meanwhile, the FPC used by the present invention can guarantee electric connection as well as convenience assemblage. The FPC has flexibility. Therefore, dimensional errors or external force are less likely to affect the performance of electric-conduction-directed soldering. Thus is further improved the stability of electric conduction-directed soldering.

It should be explained herein: the embodiments described above are only to exemplify the present invention but not to limit the scope of the present invention. It should be understood by the persons having ordinary knowledge in the field: the modifications made according to the technical schemes mentioned above or the embodiments involving partly or totally replacing the technical characteristics of the present invention would not depart from the scope of the present invention.

What is claimed is:

1. A detection package structure, comprising:
   an exterior tube;
   a detection assembly;
   a flexible printed circuit;
   a module base; and
   a lighting member disposed in the exterior tube;
   wherein the flexible printed circuit comprises:
      a main flexible plate; and
      two minor flexible plates, wherein the two minor flexible plates respectively connect with two opposite edges of the main flexible plate;
   wherein the exterior tube configured to connect with a flexible and controllable curved tube, the main flexible plate and the detection assembly are disposed on a first side of the module base, a front side of the main flexible plate is connected with a rear side of the detection assembly, a surface of the main flexible plate is provided with detection conductive materials soldered to the detection assembly for electric conduction, the detection conductive materials are further soldered to a detection wire of a cable for electric conduction via a detection wiring part;
   when being bent to various positions during operation, the two minor flexible plates are respectively on a second side and a third side of the module base, wherein the second side and the third side are opposite to each other; and a first end of each of the two minor flexible plates is provided with the lighting member, and the first end extends forward to a position near a front side of the detection assembly,
   wherein the detection assembly further comprises:
   a detection member, a wiring terminal of the detection member connected with the main flexible plate for electric conduction, and the detection member fixed to the module base;
   a detection circuit board;
   a first conductive material disposed on a first side of the detection circuit board; and
   a second conductive material disposed on a second side of the detection circuit board,
   wherein the detection circuit board is disposed in a direction substantially perpendicular to the first side of the module base, the detection member is disposed on the first side of the detection circuit board, the wiring terminal of the detection member is soldered to the first conductive material for electric conduction, the front side of the main flexible plate is connected to the second side of the detection circuit board, and the detection conductive materials.

2. The detection package structure according to claim 1, wherein a surface of each of the two minor flexible plates is provided with an illumination conductive material, the illumination conductive material is soldered to the lighting member for electric conduction to configure two of the lighting members in parallel; the illumination conductive material is soldered to an illumination wire of the cable for electric conduction via an illumination wiring part; the illumination wiring part is disposed on the main flexible plate.

3. The detection package structure according to claim 2, wherein the first side of the module base is formed with a detection positioning part for positioning and installing the detection assembly, the first side of the module base is formed with an instrument tube channel, an instrument tube passes through the instrument tube channel, and the second side and the third side of the module base are formed with a flexible plate channel for accommodating at least a portion of the two minor flexible plates.

4. The detection package structure according to claim 1, wherein each of the two minor flexible plates comprises a first plate body connected to the main flexible plate, a second plate body connected to the front side of the first plate body, and a third plate body connected to the front side of the second plate body; wherein when the first plate body, the second plate body, and the third plate body are bent to various positions during operation, the first plate body and the second plate body of one of the two minor flexible plates connect to the second side of the module base, and the first plate body and the second plate body of another one of the two minor flexible plates connect to the third side of the module base; the third plate body of the minor flexible plates is positioned on one side of a front side of the module base; and two of the third plate bodies are disposed opposite to each other.

5. The detection package structure according to claim 4, wherein if the lighting member is disposed on the surface of a side of the third plate body, which faces another one of the third plate body, a gap between two of the third plate bodies matches a corresponding-direction size of the detection assembly and that of the lighting members; and that if the lighting member is disposed on the surface of a side of the third plate body, which does not face another one of the third plate body, the gap between two of the third plate bodies matches the corresponding-direction size of the detection assembly.

6. The detection package structure according to claim 5, wherein the first side of the module base is formed with a detection positioning part for positioning and installing the detection assembly, the first side of the module base is formed with an instrument tube channel, an instrument tube passes through the instrument tube channel, and the second side and the third side of the module base are formed with a flexible plate channel for accommodating at least a portion of the two minor flexible plates.

7. The detection package structure according to claim 4, wherein the first side of the module base is formed with a detection positioning part for positioning and installing the detection assembly, the first side of the module base is formed with an instrument tube channel, an instrument tube passes through the instrument tube channel, and the second side and the third side of the module base are formed with a flexible plate channel for accommodating at least a portion of the two minor flexible plates.

8. The detection package structure according to claim 1, wherein the first side of the module base is formed with a detection positioning part for positioning and installing the detection assembly, the first side of the module base is formed with an instrument tube channel, an instrument tube passes through the instrument tube channel, and the second side and the third side of the module base are formed with a flexible plate channel for accommodating at least a portion of the two minor flexible plates.

9. The detection package structure according to claim 1, wherein at least a portion of an outer edge of the detection circuit board and at least a portion of the outer edge of the module base are in the shape of a circular arc and match an inner wall of the exterior tube.

10. The detection package structure according to claim 1, wherein the main flexible plate and/or the minor flexible plates are bonded to the module base with glue.

11. An in vivo detection apparatus, comprising:
a flexible and controllable curved tube and the detection package structure according to claim 1; wherein the detection package structure forms an insertion portion at one side of the controllable curved tube.

12. The in vivo detection apparatus according to claim 11, wherein the surface of each of the two minor flexible plates is provided with an illumination conductive material, the illumination conductive material is soldered to the lighting members for electric conduction to configure two of the lighting members in parallel; the illumination conductive material is soldered to a illumination wire of the cable for electric conduction via a illumination wiring part; the illumination wiring part is disposed on the main flexible plate.

13. The in vivo detection apparatus according to claim 11, wherein each of the two minor flexible plates comprises a first plate body connected to the main flexible plate, a second plate body connected to the front side of the first plate body, and a third plate body connected to the front side of the second plate body;
wherein when the first plate body, the second plate body, and the third plate body are bent to various positions during operation, the first plate body and the second plate body of one of the two minor flexible plates connect to the second side of the module base, and the first plate body and the second plate body of another one of the two minor flexible plates connect to the third side of the module base; the third plate body of the minor flexible plates is positioned on one side of the front side of the module base; and two of the third plate bodies are disposed opposite to each other.

14. The in vivo detection apparatus according to claim 11, wherein if the lighting member is disposed on the surface of a side of a third plate body, which faces another one of the third plate body, the gap between two of the third plate bodies matches the corresponding-direction size of the detection assembly and that of the lighting members; and that if the lighting member is disposed on the surface of a side of the third plate body, which does not face another one of the third plate body, the gap between two of the third plate bodies matches the corresponding-direction size of the detection assembly.

15. The in vivo detection apparatus according to claim 11, wherein the first side of the module base is formed with a detection positioning part for positioning and installing the detection assembly, the first side of the module base is formed with an instrument tube channel, an instrument tube passes through the instrument tube channel, and the second side and the third side of the module base are formed with a flexible plate channel for accommodating at least a portion of the two minor flexible plates.

* * * * *